United States Patent [19]
Cho

[11] Patent Number: 5,882,884
[45] Date of Patent: Mar. 16, 1999

[54] EXPRESSION OF PROTEINACEOUS SWEETENERS IN YEAST

[75] Inventor: Joong Myung Cho, Concord, Calif.

[73] Assignee: Lucky Biotech Corporation, Daejeon, Rep. of Korea

[21] Appl. No.: 837,541

[22] Filed: Feb. 14, 1992

Related U.S. Application Data

[63] Continuation of Ser. No. 291,456, Dec. 29, 1988, abandoned, which is a continuation-in-part of Ser. No. 64,341, Jun. 19, 1987, abandoned.

[51] Int. Cl.$^6$ .............................. C12P 21/02; C12N 1/19; C12N 15/81
[52] U.S. Cl. ................ 435/69.1; 435/252.3; 435/254.11; 435/254.2; 435/254.21; 435/320.1
[58] Field of Search ................... 435/69.1, 252.3, 435/70, 320.1, 254.11, 254.2, 254.21

[56] References Cited

U.S. PATENT DOCUMENTS

| | | | |
|---|---|---|---|
| 3,998,798 | 12/1976 | Cagan et al. | 530/300 |
| 4,546,082 | 10/1985 | Kurjan et al. | 435/172.3 |
| 4,657,857 | 4/1987 | Edame et al. | 435/69.1 |
| 4,661,454 | 4/1987 | Botstein et al. | 435/69.1 |
| 4,774,180 | 9/1988 | Toth et al. | 435/69.7 |
| 4,929,553 | 5/1990 | Bussey et al. | 435/69.1 |

OTHER PUBLICATIONS

Itakura et al. Science 158:1056–1063. 1977.
Bohak et al. Biochemica et Biophysica Acta 427:153–170 1976.
Hudson et al. Biochem. & Biophys. Res. Comm. 71(1) 212–220 (1976).
Powells et al. Cloning Vechors Elsevier New York 1985.
Morris et al., *Journal of Biological Chemistry* (1973) 248:534–539.
Robert Cagan in *Science* 181:32–35.
Wlodawer and Hodgson, *Proc. Nat. Acad. Sci. USA* (1975) 72:398–399.
Bohak and Li in *Biochimica et Biophysic Acta* (1976) 427:153–170.
Hudson and Biemann in *Biochemical and Biophysical Research Communications*, (1976) 71:212–220.
Van Der Wel and Loeve in *Febs Letters* (1973) 29:181–184.
B. Jirgensons in *Biochimica et Biophysica Acta* (1976) 446:255–261.

*Primary Examiner*—David Guzo
*Attorney, Agent, or Firm*—Bertram I. Rowland; Flehr Hohbach Test Albritton & Herbert

[57] ABSTRACT

A yeast expression system is provided for expressing novel protein sweeteners. The construct provides for secretion of the protein sweeters into a form which can be readily purified and isolated, providing an active product.

21 Claims, No Drawings

EXPRESSION OF PROTEINACEOUS SWEETENERS IN YEAST

CROSS REFERENCE TO RELATED APPLICATIONS

This application is a CONTINUATION of U.S. Application Ser. No. 07/291,456 filed Dec. 29, 1988, now abandoned, which is a Continuation in Part of U.S. application Ser. No. 064,341 filed Jun. 19, 1987 now abandoned.

TECHNICAL FIELD

The field comprises recombinant methods for production of synthetic proteinacious sweeteners and compositions.

BACKGROUND

Monellin is an intensely sweet material present in the sap of "Serendipity Berries," the fruit of the West African plant, *Dioscoreophyllum comminisii*. The material has been purified to homogeneity and shown to be a basic protein with a molecular weight of about $1.1 \times 10^4$ and is completely free of carbohydrate. Monellin is the first well characterized material among several sweet or taste modifying substances found in tropical plants. It has been characterized and shown to have two subunits of about the same size held together by non-covalent bonds. The two subunits are not identical and the flavor modifying ability of monellin is dependent upon the presence of both subunits and a single mercaptan group, which if blocked abolishes the sweetness.

Because of the uncertainties and cost of extracting natural products from plant sources, an alternative route to the production of protein sweeteners is of substantial interest. Recombinant techniques offer an opportunity to synthesize proteins of varying types. However, in employing recombinant techniques, one is required to develop a strategy for producing the gene, demonstrate successful expression of the protein in a cellular host, and isolate a product which is shown to have physiological activity. In many instances, it is necessary or desirable to modify the naturally occurring sequence, which substantially increases the uncertainties of success of the production of a useful product.

Relevant Literature

Morris et al., *J. Biol. Chem.* (1973) 248:534–439 describe the characterization of monellin. See also Cagan, *Science* (1973) 181:32–35; Wlodawer and Hodgson, *Proc. Natl. Acad. Sci. USA* (1975) 72:398–399; Bohak and Li, *Biochimica et Biophysica Acta* (1976) 427:153–170; Hudson and Bieman, *Biochem. Biophys. Res. Comm.* (1976) 71:212–220; Jirgenson, *Biochim. Biophys. Acta* (1976) 446:255–261; and Van der Wel and Loeve, *FEBS Lett.* (1973) 29:181–183 for further characterization. U.S. Pat. No. 3,998,798 describes the preparation of natural monellin.

Yeast leader sequences are described by Stack et al., *Nucl. Acids Res.* (1984) 12:6011–6030 and Julius et al., *Cell* (1984) 37:1075–1089. The GAL upstream activating sequence, a cis-acting DNA element, is described in Johnston and Davis, *Mol. Cell. Biol.* (1984) 4:1440–1448, while the transcription initiation region of glyceraldehyde-3-phosphate dehydrogenase is described by Holland and Holland, *J. Biol. Chem.* (1979) 254:5466–5475; 9839–9845; and Holland et al., ibid., (1983) 258:5291–5299.

SUMMARY OF THE INVENTION

Methods and compositions are provided for the production of novel proteinaceous sweeteners, where the resulting sweeteners are expressed in a yeast host and secreted in high yield in an active conformation.

DESCRIPTION OF SPECIFIC EMBODIMENTS

Novel methods are provided for producing synthetic monellin having altered wild type sequences as a result of a bridge between the A(I) and B(II) subunits and at least one lesion involving at least one amino acid substitution. Constructs are provided which employ a strong transcriptional initiation region, particularly where the region is a hybrid comprising a 3' domain of a strong yeast transcription initiation region and a 5' domain which enhances the transcriptional activity of the 3' domain.

The DNA constructs employed for the expression of the subject sweeteners will comprise in the 5'–3' direction of transcription, the transcriptional initiation region, an open reading frame comprising an initiation codon, optionally, a signal sequence, which provides for secretion and processing, so as to remove the signal sequence and produce a mature peptide product, and a transcriptional termination region, where the initiation region and termination region are functional in yeast.

The transcriptional initiation region may be a naturally ocurring region or preferably selected, so as to have two domains: A 5' domain which will serve as an enhancer and regulatory region, which may be induced by an external agent; and a 3' domain which will serve to provide for transcriptional initiation, directing the initiation site for the yeast RNA polymerase. The 5' domain may be any domain which provides for enhancement and regulation, that is, domains which provide for inducible regulation, such as heat shock genes, metallothionein genes, metabolite induced genes, and the like. Of particular interest is the GAL1,10 regulatory region, particularly the upstream activating sequence, which can be induced by employing galactose as the sole carbon source, after the host cells have been grown to high density with a different carbon source. Generally, the 5' domain will be at least 50 bp, more usually at least 75 bp and may be 500 bp or more, although usually the regulatory region will not be greater than about 1 kbp. The sequence associated with the inducible regulation of transcription will generally be within about 400 bp, more usually within about 250 bp of the 3' domain.

The 3' domain or the promoter region without the 5' domain may be any strong yeast functional transcriptional initiation region or promoter. Conveniently, any of the glycolytic enzyme initiation regions may be employed, such as alcohol dehydrogenase I or II, glyceraldehyde-3-phosphate dehydrogenase, glucose-6-phosphate dehydrogenase, pyruvate kinase, triose isomerase, phosphoglucose kinase, etc. Of particular interest is the glyceraldehyde-3-phosphate dehydrogenase. Other promoter regions include the α-amylase region, invertase region, alkaline phosphatase region, etc. The 3' domain will usually be at least about 150 bp, more usually at least about 250 bp, and usually not more than about 1.5 kbp, more usually not more than about 2 kbp. The 3' domain will usually be within about 200 bp of the initiation codon, more usually within about 150 bp of the initiation codon.

The two regions may be ligated together by any convenient means. Where convenient sites exist, these may be employed. In the absence of convenient restriction sites, in vitro mutagenesis or primary repair may be employed. Alternatively, in the absence of convenient restriction sites, alternative restriction sites may be employed and the two domains joined by use of an adaptor.

The coding region will comprise in the 5'–3' direction of transcription, the initiation codon as part of a signal sequence for secretion of the subject product, a processing signal, which provides for removal of the signal sequence and processing signal to provide the mature peptide product, and the coding region encoding the mature peptide product.

The coding sequence will usually provide for the joining of monellin subunit B(II) at the N-terminus to subunit A(I) as the C-terminus of the protein. (In referring to the subunits, both the natural and mutated subunits are intended.) The region of joining may be varied and may involve the amino acids adjacent to the junction, where one or more amino acids may be changed.

The two subunits may be joined by a short bridge, usually of not more than 10, usually of not more than 8 amino acids, or may be joined directly without intervening amino acids, or preferably the amino acids at the juncture will be modified. The amino acids at the juncture forming the bridge will provide for a polar juncture, that is, at least 50 number %, usually at least about 75 number % of the amino acids will be polar and conveniently, at least about 25 number %, generally about 50 number % will be amino acids naturally present at the subunit terminal. The amino acids may come from a loop of subunits I and II.

In referring to the juncture, the juncture will include as a bridge not more than about 10, usually not more than about 6 amino acids of the naturally occurring sequence of the subunits. For the joining of the C-terminus of subunit II with the N-terminus of subunit I, the juncture will be at Ile(46) of subunit II and Gly(6) of subunit I with the intervening amino acids, if any, as the bridge.

Where subunit II is the N-terminus, one or more of the wild-type amino acids at the juncture may be removed or substituted from either or both of the subunits, usually not more than about a total of 12 amino acids, more usually not more than about a total of 10 amino acids will be removed or substituted, more usually not more than about a total of about 6 amino acids, where the number of amino acids for each subunit will be not more than about 8, usually not more than about 6. Generally not more than 75% of the removed or substituted amino acids will be associated with one of the subunits.

Bridges of interest will include:

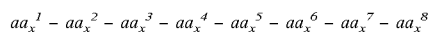

where only one amino acid need be present, and the individual amino acids as defined are as follows:

$aa^1$ is A, D, E, K, R, or Y;
$aa^2$ is Y, A, D, E, N, Q, R, T, or S;
$aa^3$ is N, Q, S, T, D, E, R, or Y;
$aa^4$ is F, W, Y, S, T, D, E, K or R;
$aa^5$ is D, E, K, R, L or T;
$aa^6$ is D, E, V, I, L, K or R;
$aa^7$ is G, A, V, I, L, K or R;
$aa^8$ is K or R;

where x is 0 or 1, at least one x being 1.

Compositions of interest include sequences where:

$aa^1$ is Y or E;
$aa^2$ is D, E, Y or K;
$aa^3$ is N, T, A or Y;
$aa^4$ is R, S, K or E;
$aa^5$ is E, D or T;
$aa^6$ is K, D or R;
$aa^7$ is G, I or L;
$aa^8$ is K or R;

For sequences having the first two amino acids Y and E, there may be from 0 to 4x's that are 0, while for chains having different amino acids as the first two amino acids there may be from 0 to 5x's that are 0. That is, the above chains will usually be from 3 to 8, more usually 4 to 8, amino acids.

Of particular interest is removal of the naturally occurring phenylalanine, where the juncture will be Y-E-N-E-R-E-I-K. Other bridges include Y-E-N-R-E-D-I-K; Y-K-T-R-E-D-I-K; Y-E-R-E-I-K; Y-E-N-I-K; Y-E-I-K; Y-Y-A-S-D-K-L-K; Y-A-S-D-K-L; Y-A-S-D-K; Y-S-D-K; E-D-Y-K-T-R-G-R; and E-D-Y-T-R. Usually there will be at least one Y, E, D, K or R present in the chain, more usually at least one E, D, K or R. Preferred amino acids for the bridge are Y, I, S, T, D, E, K, R, N or Q, where greater than 50% of the amino acids of the bridge will be selected from this group.

In addition to any changes at the juncture, there will be at least one lesion, that is, a substitution, deletion, or insertion of one of the subunits, where the result is to reduce the pI or increase sweetness. The pI or ionization constant can be reduced by substitution of a basic amino acid with an acidic or neutral amino acid, preferably an acidic amino acid, by deleting a basic amino acid, or by inserting an acidic amino acid. Usually, the number of lesions will be fewer than 8, usually fewer than 6, preferably fewer than about 4, where a lesion is a single amino acid substitution, insertion or deletion.

Of particular interest is the substitution of lysine at positions 17 or 43 with an acidic amino acid, e.g. aspartic or glutamic acid, particularly glutamic, while of less interest is substitution of arginine at position 70 or 86. Desirably, the substitutions should result in a pI of less than about 8 (monellin has a pI of 9.3), preferably less than about 7.5, particularly in the range of about 6–7.5, more usually in the range of about 6.5–7.5.

Any convenient termination region may be employed which is functional in yeast. The transcriptional termination region may be from the same gene as the 3' domain of the transcriptional initiation region or other gene, such as the genes indicated as useful for the transcriptional initiation region. The choice of termination region is primarily one of convenience.

The expression construct may be joined to any convenient vector for cloning. Usually, during the synthesis of the construct, various fragments, will be cloned, the fragments isolated and analyzed, joined together, recloned, and the like. The final construction may involve a shuttle vector, which provides for replication in both a bacterium, *E. coli*, and yeast.

A variety of vectors functional in yeast are available or can be readily prepared, based on vectors which have been disclosed in the literature. Conveniently, the vector may have a stable replication system for replication in the yeast host or an unstable replication system or no replication system, for integration into the genome of the yeast host. Vectors which are employed may include the 2 µm plasmid replication system, a combination of a centromere, e.g. CEN3 and an ARS, or the like. For integration, only a selectable marker may be employed.

The vector will also provide for a marker which provides for selection of the host containing the construct. Markers will usually employ antibiotic resistance or impart prototrophy to an auxotrophic host. Antibiotic resistance may be to kanamycin, chloramphenicol, tetracycline, ampicillin, etc. One of more markers may be present, particularly where different markers are used for the different hosts.

The yeast hosts may include strains of Saccharomyces, particularly *cerevisiae*, Schizosaccharomyces, Kluyveromyces, e.g. *lactis*, Candida, etc. Desirably, industrial strains are employed which have been shown to be stable in fermentation.

Depending upon the nature of the host, various techniques may be employed for transforming the expression host with the expression cassette, either by itself, or as part of a vector or other construct. The introduction of the expression cassette may be as a result of transformation which includes conjugation, transformation, transfection, and transduction; or fusion, etc. Intact host cells, protoplasts, partially regenerated protoplasts, or the like may be employed for the introduction of the exogenous DNA.

Once the host has been transformed, it may then be grown in a selective medium, so as to select for those hosts having the marker or associated expression cassette. Where antibiotic resistance is involved, the nutrient may contain a level of the antibiotic which is cytotoxic in the absence of the antibiotic resistance gene. In the case of auxotrophy complementation, the nutrient medium lacks the necessary metabolite.

Where the product is produced and retained in the cytoplasm, after sufficient time for the cells to grow, the cells may be lysed and the desired protein obtained by conventional purification procedures. These procedures include liquid-liquid extraction, HPLC, chromatography, electrophoresis, etc. The product may then be subjected to further purification, such as gel exclusion, chromatography, etc.

The resulting product may be used in a variety of ways as a sweetener. It may be used in canned products, in conjunction with various carbonated drinks, as a powder or liquid for addition to various beverages, such as coffee, tea, or the like, in cooking, chewing gum, toothpaste, mouthwash, dental hygiene products, pharmaceuticals, meat products, e.g. ham, sausage, etc., instant soups, yogurt, desserts, cereals, animal food, etc.

The subject proteinaceous sweeteners may be formulated as a liquid or powder. As a liquid, other additives may be combined, such as stabilizers, buffers, bactericides, protease inhibitors, or the like. An aqueous medium will normally be used where the sweetener will be from about 0.1 to 90 weight % of the composition. For powders, various excipients may be added which are conventional food extenders.

The following examples are provided by way of illustration and not by way of limitation.

EXPERIMENTAL

1. Oligonucleotide Synthesis, Purification, and Oligomerization of Inducible Galgap Hybrid Promoter The oligonucleotides shown in FIG. 1 were prepared based on published sequences of the GAL upstream activating sequence, a cis-acting DNA element, and yeast glyceraldehyde-3-phosphate dehydrogenase

FIGURE 1
SYNTHETIC OLIGOMERS OF GALGAP HYBRID PROMOTER GENE

```
U1:  5'-GATCC AAAAT CATCG CTTCG CTGAT TAATT ACCCC AGAAA TAAGG-3'                  (45mer)
U2:  5'-CTAAA AAACT AATCG CATTA TCATC CTATG GTTGT TAATT TGATT CGT-3'              (48mer)
U3:  5'-TCATT TGAAG GTTTG TGGGG CCAGG TTACT GCCAA TTTTT CCTCT TCA-3'              (48mer)
U4:  5'-TAACC ATAAA AGCTA GTATT GTAGA ATCTT TATTG TTCGG AGCAG TGCG-3'             (49mer)
U5:  5'-GCGCG AGGCA CATCT GCGTT TCAGG AACGC GACCG GTGAA GACGA GGA-3'              (48mer)
U6:  5'-CGCAC GGAGG AGAGT CTTCC TTCGG AGGGC TGTCA CCCGC TCGGC GGCTT-3'            (50mer)
U7:  5'-CTAAT CCGTT ATTCC CCTAC TTGAC TAATA AGTAT ATAAA GACGG TAG-3'              (48mer)
U8:  5'-GTATT GATTG TAATT CTGTA AATCT ATTTC TTAAA CTTCT TAAAT TCTA-3'             (49mer)
U9:  5'-CTTTT ATAGT TAGTC TTTTT TTTAG TTTTA AAACA CCAAG-3'                        (40mer)
U10: 5'-AACTT AGTTT CGAAT AAACA CACAT AAACA AACAC C-3'                            (36mer)

L1:  3'-GTTTT AGTAT CGAAG CGACT AATTA ATGGG GGTCT TTATT CCGAT TTTTT GATTA GCGTA-5' (60mer)
L2:  3'-ATAGT AGGAT ACCAA CAATT AAACT AAGCA AGTAA ACTTC CAAAC ACCCC GGTCC-5'       (55mer)
L3:  3'-AATGA CGGTT AAAAA GGAGA AGTAT TGGTA TTTTC GATCA TAACA TCTTA-5'             (50mer)
L4:  3'-GAAAT AACAA GCCTC GTCAC GCCGC GCTCC GTGTA GACGC AAAGT C-5'                 (46mer)
L5:  3'-CTTGC GCTGG CCACT TCTGC TCCTG CGTGC CTCCT CTCAG AAGGA AGCC-5'              (49mer)
L6:  3'-TCCCG ACAGT GGGCG AGCCG CCGAA GATTA GGCAA TAAGG GGATG AACTG-5'             (50mer)
L7:  3'-ATTAT TCATA TATTT CTGCC ATCCA TAACT AACAT TAAGA CATTT AGA-5'               (48mer)
L8:  3'-TAAAG AATTT GAAGA ATTTA AGATG AAAAT ATCAA TCAGA AAAAA AATCA-5'             (50mer)
L9:  3'-AAATT TTGTG GTTCT TGAAT CAAAG CTTAT TTGTG TGTAT TTGTT TGTGG TACC-5'        (54mer)
```

LIGATION STRATEGY OF GALGAP HYBRID PROMOTER GENE

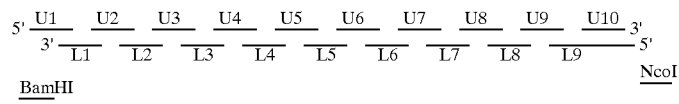

sequences employing an Applied Biosystems DNA synthesizer model 380 B. Each oligomer was isolated from 8M urea-polyacrylamide gel and purified with Sep-pack C18 Column (Whatman Co.).

Each oligomer was phosphorylated at 37° C. for 45 min in a reaction mixture of 38 μl containing 50 mM Tris-HCl, pH 8.0, 10 MgCl$_2$, 10 mM DTT, 1 mM ATP, 5 units of T4 polynucleotide kinase. The reaction mixes were pooled, extracted with an equal volume of phenol/chloroform, precipitated with 2.5 volumes of ethanol and dried under vacuum. After dissolving the dried pellet in 15 μl of distilled water and 7 μl of ligation buffer containing 0.2 mM Tris-HCl, pH 7.5, 0.1M MgCl$_2$, and 0.1 mM DTT, the solution was placed in a 90° C. water bath and cooled slowly to room temperature overnight. To the mixture was then added 7 μl of 10 mM ATP, 40 units of T4 DNA ligase and 2 μl of distilled water. After allowing the reaction mixture to stand at room temperature for 10 min, the DNA was extracted by phenol/chloroform, precipitated and dried as described above. The solid residue was then dissolved in 85 μl of distilled water and digested with BamHI and NcoI. The 462 bp fragment was isolated by 7% acrylamide gel electrophoresis, electroeluted and purified on an elutip-D column (Schleicher and Schuell Co.).

2. Molecular Cloning and DNA Sequencing of Galgap Hybrid Promoter

M13rp9 RF, a derivative of M13mp19, which has an NcoI site between EcoRI and KpnI of M13mp19, was used for cloning the galgap hybrid promoter gene. The gel isolated BamHI-NcoI fragment of galgap hybrid DNA was combined with NcoI-BamHI digested M13rp9 RF in 10 μl of 20 mM Tris-HCl, pH 7.5, 10 mM magnesium chloride, 10 mM DTT and 200 units of T4 DNA ligase, and the ligation mixture incubated at 4° C. overnight. Transformation of *E. coli* JM 101 competent cells was achieved by adding 5 μl of a ligation mixture to 200 μl of the cells and the dideoxy DNA sequencing and M13rp9-GG RF ligation product preparation were done as described by Messing, *Methods in Enzymology* (1983) 101:20–78; Sanger et al. *Proc. Natl. Acad. Sci. USA* (1985) 74:5463–5467. The promoter region had the sequence shown in FIG. 2.

| FIG. 2 | | | | |
|---|---|---|---|---|
| galgap | | | | |
| 10 | 20 | 30 | 40 | 50 |
| GATCAAAAAT | CATCGCTTCG | CTGATTAATT | ACCCCAGAAA | TAAGGCTAAA |
| 60 | 70 | 80 | 90 | 100 |
| AAACTAATCG | CATTATCATC | CTATGGTTGT | TAATTTGATT | CGTTCATTTG |
| 110 | 120 | 130 | 140 | 150 |
| AAGGTTTGTG | GGGCCAGGTT | ACTGCCAATT | TTTCCTCTTC | ATAACCATAA |
| 160 | 170 | 180 | 190 | 200 |
| AAGCTAGTAT | TGTAGAATCT | TTATTGTTCG | GAGCAGTGCG | GCGCGAGGCA |
| 210 | 220 | 230 | 240 | 250 |
| CATCTGCGTT | TCAGGAACGC | GACCGGTGAA | GACGAGGACG | CACGGAGGAG |
| 260 | 270 | 280 | 290 | 300 |
| AGTCTTCCTT | CGGAGGGCTG | TCACCCGCTC | GGCGGCTTCT | AATCCGTTAT |
| 310 | 320 | 330 | 340 | 350 |
| TCCCCTACTT | GACTAATAAG | TATATAAAGA | CGGTAGGTAT | TGATTGTAAT |
| 360 | 370 | 380 | 390 | 400 |
| TCTGTAAATC | TATTTCTTAA | ACTTCTTAAA | TTCTACTTTT | ATAGTTAGTC |
| 410 | 420 | 430 | 440 | 450 |
| TTTTTTTAG | TTTAAAACA | CCAAGAACTT | AGTTTCGAAT | AAACACACAT |
| 460 | | | | |
| AAACAAACAC | CATGG | | | |

Cassette Construction For Protein Sweetener Gene Expression

The synthetic galgap hybrid DNA promoter (462 bp) was isolated from M13rp9 RF-galgap and purified with a 7% polyacrylamide gel as described above. The protein sweetener gene which was synthesized, cloned and expressed in *E. coli*, was isolated from the ptrp-MON-1 plasmid by digestion with ClaI and SalI to obtain a partial protein sweetener gene fragment. (See U.S. application Ser. No. 064341, filed Jun. 19, 1987, now abandoned.)

Fused Monellin

| | | | | | | | | | 10 | | | | | |
|---|---|---|---|---|---|---|---|---|---|---|---|---|---|---|
| Gly | Glu | Trp | Glu | Ile | Ile | Asp | Ile | Gly | Pro | Phe | Thr | Gln | Asn | Leu |
| | | | | 20 | | | | | | | | | | 30 |
| Gly | Lys | Phe | Ala | Val | Asp | Glu | Glu | Asn | Lys | Ile | Gly | Gln | Tyr | Gly |
| | | | | | | | | | 40 | | | | | |
| Arg | Leu | Thr | Phe | Asn | Lys | Val | Ile | Arg | Pro | Cys | Met | Lys | Lys | Thr |
| | | | | 50 | | | | | | | | | | 60 |
| Ile | Tyr | Glue | Asn | Glu | Arg | Glu | Ile | Lys | Gly | Tyr | Glu | Tyr | Gln | Leu |
| | | | | | | | | | 70 | | | | | |
| Tyr | Val | Tyr | Ala | Ser | Asp | Lys | Leu | Phe | Arg | Ala | Asp | Ile | Ser | Glu |
| | | | | 80 | | | | | | | | | | 90 |
| Asp | Tyr | Lys | Thr | Arg | Gly | Arg | Lys | Leu | Leu | Arg | Phe | Asn | Gly | Pro |
| Val | Pro | Pro | Pro | | | | | | | | | | | |

A synthetic adapter for the NcoI/ClaI fragment of N-terminal of protein sweetner gene was synthesized with the following sequence.

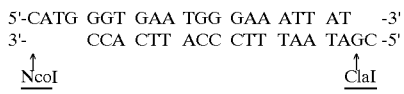

Plasmid pLBC is a derivative of pBR322 and prepared as follows. After digesting pBR322 of EcoRI and SalI, the sites were converted to BamHI sites by inserting a synthetic linker to provide a pBR322 with a single BamHI site. Plasmid pGAP, which is a derivative of pLBC in which 1300 base pairs of the BamHI fragment containing a glyceraldehyde-3-phosphate dehydrogenase (GAP) gene (Holland and Holland, supra; Holland et al., supra) promoter and terminator were inserted at the BamHI site of PLBC. The resulting vector (pGAP) comprises about 400 bp of GAP promoter, the 5' untranslated region of the GAP gene and about 900 bp of GAP terminator, the 3' untranslated region of the GAP gene. These two fragments were linked using a synthetic adapter (33 mer, 5'-CCA TGG GGT ACC CGG GGA TCC TCT AGA GTC GAC-3') for the NcoI site at the GAP initiator methionine at one end and the SalI site at the other end for the natural SalI site of the 3' untranslated region of the GAP gene. A SalI-BamHI fragment containing about 900 bp of GAP terminator was obtained from pGAP and isolated from a 1% agarose gel.

A ClaI-SalI fragment from ptrp322H MON-1 carrying the sweetener gene, an NcoI-ClaI adapter, (see above), a BamHI-NcoI 462 bp fragment from M13rp9-GG providing the galgap promoter region, and a SalI-BamHI partial digestion fragment (about 4.5 Kbp) comprising about 900 bp of the GAP terminator region were ligated together to form an expresion cassette and cloned into pLBC to provide pGG-MON. The expression cassette excised from pGG-MON with BamHI was inserted into the BamHI site of pYLBC, an E. coli-yeast shuttle vector (pYLBC is a derivative of pJDB219 (Beggs, Nature (1978) 275:104–109) in which the region corresponding to bacterial plasmid was replaced by the entire pBR322). The plasmid pYLBC has a complete yeast 2 µm replication system and the yeast LEU2 gene. The resulting plasmid was named pYGG-MON.

DNA Synthesis and Construction of a Secretion Cassette

A yeast leader sequence and processing signal was synthesized based on the sequence described by Stack et al., Nucleic Acids Res. (1984) 12:6011–6030 and Julius et al., Cell (1984) 37:1075–1089. The DNA sequence as confirmed by the M13 dideoxy DNA sequencing method is as follows:

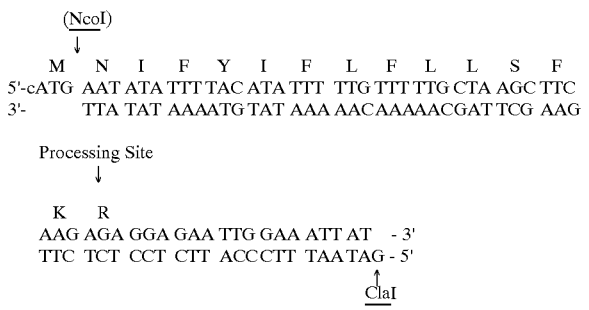

The 63 bp fragment of leader and processing signal sequences was isolated from 8M urea-acrylamide gel and ligated with NcoI-ClaI digested plasmid pGG-MON (see above) in the presence of 50 mM Tris-HCl, pH 8.0, 10 mM DTT, 1 mM ATP and 5 units of T4 DNA ligase to provide pGGKL-MON. The recombinant secretion vector was obtained after screening of E. coli HB101 transformants. The secretion cassette was excised by digestion of pGGKL-MON with BamHI and the fragment ligated into the BamHI site of pYLBC to provide pYGGKL-MON.

Yeast Transformation, Growth and Secretion of Protein Sweetener

Saccharomyces cerevisiae DC04 (α MAT ade1 leu2), DBY746 (MAT α, his3-1, leu2-3, leu2-112, ura3-52, trp1-289) were obtained from the Yeast Genetic Stock Center (University of California, Berkeley, Calif.). Plasmid DNA (pYGGKL-MON) was introduced into yeast cells as described by Hinnen, et al., Proc. Natl. Acad. Sci U.S.A. (1978) 75:1929–1933. The transformants were grown overnight in 3 ml culture medium containing synthetic medium deficient in leucine (Sherman, et al., Methods in Yeast Genetics, Cold Spring Harbor Laboratory, Cold Spring Harbor, N.Y., 1982). The overnight culture was inoculated in YEPD medium (20 g Bactopeptone, 10 g yeast extracts, 20 g glucose per liter) and grown to an O.D.650 nm of around 10. Galactose was added to provide a final concentration of 2% in the culture and the culture incubated further until an O.D. 650 nm of around 25 was obtained.

Identification of a Protein Sweetener Internally Expressed or Secreted from Saccharomyces cerevisiae To the induced cell suspension (100 µl) or culture supernant (100 µl), 50 µl of 3× protein SDS-sample buffer (60 mM Tris-HCl, pH 6.8, 2.3% SDS, 10% glycerol, 2% β-mercaptoethanol) was added. The mixture was boiled for 5 min and 10 µl loaded onto a 15% SDS-polyacrylamide gel (Laemmli, Nature (1977) 227:680–685). The gel was stained with 0.05% Coomassie brilliant blue R-250 in methanol/acetic acid/water (4:1:5, v/v), and destained in the same solution without dye. The gel showed a band of a protein of about the correct molecular weight (11 kilodalton) which band was absent in a sample from a control culture.

An effective expression system is provided for producing novel protein sweeteners. The products are secreted, so as to be really isolatable and purified which provides for a protein used as a food additive for sweetening a wide variety of products. The products fold properly, so as to be obtained in active form, without requiring extensive renaturation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for preparing a protein sweetener comprising an amino acid sequence of the monellin subunits joined together by a bridge wherein said sequence is modified by a mutation in the native sequence at other than the bridge, said method comprising:

growing in a culture medium of yeast cells comprising a DNA sequence which comprises in the direction of transcription, a transcriptional initiation region comprising a 5' domain from the 5' domain of a transcriptional initiation region of an inducible gene functional in yeast and the 3' domain of a yeast initiation region, an open reading frame under the transcriptional regulation of said initiation region comprising a signal sequence, processing signal and a structural gene encoding said protein sweetener comprising a sequence of monellin subunit I and subunit II joined together by a bond or bridge, and where the monellin sequence comprises a non-conservative substitution, and a transcriptional termination region; and wherein the expression product of said gene is processed and secreted into said medium; and isolating said protein sweetener.

2. A method according to claim 1, wherein said 3' domain is the 3' domain of a yeast glycolytic enzyme.

3. A method according to claim 1, wherein said inducible 5' domain is a metabolite inducible domain.

4. A method according to claim 1, wherein said yeast is *Saccharomyces cerevisiae.*

5. A method according to claim 2, wherein said yeast glycolytic enzyme is glyceraldehyde-3-phosphate dehydrogenase.

6. A method according to claim 3, wherein said metabolite is D-galactose.

7. A method for preparing a protein sweetener comprising an amino acid sequence of the monellin subunits joined together by a bridge wherein said sequence is modified by a mutation in the native sequence of the protein sweetener, said method comprising:

growing in a nutrient medium a *Saccharomyces cerevisiae* yeast culture of yeast cells comprising a DNA construct comprising in the direction of transcription, a transcriptional initiation region comprising a 5' domain from the 5' domain of the transcriptional initiation region of an inducible gene functional in yeast and the 3' domain of a yeast glycolytic gene initiation region, an open reading frame under the transcriptional regulation of said initiation region comprising a signal sequence, processing signal and a structural gene encoding said protein sweetener comprising a sequence of monellin subunit I and subunit II joined together by a bond or bridge, and the monellin sequence comprises a substitution, and a transcriptional termination region;

wherein the expression product of said gene is processed and secreted into said medium; and isolating said protein sweetener.

8. A method according to claim 7, wherein said 3' domain is the 3' domain of a yeast dehydrogenase enzyme gene.

9. A method according to claim 7, wherein said inducible 5' domain is a metabolite inducible domain.

10. A method according to claim 8, wherein said yeast dehydrogenase enzyme is glyceraldehyde-3-phosphate dehydrogenase.

11. A method according to claim 9, wherein said metabolite is D-galactose.

12. A yeast cell comprising a DNA construct comprising in the 5'→3' direction of transcription a transcriptional initiation region comprising a 5' domain from the 5' domain of the transcriptional initiation region of an inducible gene functional in yeast and the 3' domain of a yeast initiation region, an open reading frame under the transcriptional regulation of said initiation region comprising a signal sequence, processing signal and a structural gene encoding a protein sweetener comprising a sequence of monellin subunit I and subunit II joined together by a bond or bridge, and the monellin sequence comprises a non-conservative substitution, and a transcriptional termination region.

13. A yeast cell according to claim 12, wherein said 3' domain is the 3' domain of a yeast glycolytic enzyme.

14. A yeast cell according to claim 12, wherein said inducible 5' domain is a metabolite inducible domain.

15. A yeast cell according to claim 12, wherein said yeast is *Saccharomyces cerevisiae* and said transcriptional initiation region comprises a 5' domain from a GAL upstream activating sequence and a 3' domain from glyceraldehyde-3-phosphate dehydrogenase.

16. A yeast cell according to claim 13, wherein said yeast glycolytic enzyme is glyceraldehyde-3-phosphate dehydrogenase.

17. A yeast cell according to claim 14, wherein said metabolite is D-galactose.

18. A DNA expression construct comprising in the 5'–3' direction of transcription a 5' domain from the 5' domain of the transcriptional initiation region of an inducible gene functional in yeast and the 3' domain of a yeast initiation region, an open reading frame under the transcriptional regulation of said initiation region comprising a signal sequence, processing signal and a structural gene encoding a protein sweetener comprising a sequence of monellin subunit I and subunit II joined together by a bond or bridge, and the monellin sequence comprises a non-conservative substitution, and a transcriptional termination region.

19. A DNA expression construct according to claim 18, wherein said transcriptional initiation region comprises a 5' domain from a GAL upstream activating sequence and a 3' domain from a glyceraldehyde-3-phosphate dehydrogenase promoter.

20. A DNA expression construct according to claim 19, wherein said signal sequence is the partial signal sequence of *Kluveromyces lactis* killer toxin and said processing signal is lys-arg.

21. A vector which stably replicates in a yeast cell comprising a DNA expression construct according to any of claims 18–20.

* * * * *